United States Patent
Sloman

(10) Patent No.: US 6,658,295 B1
(45) Date of Patent: Dec. 2, 2003

(54) METHOD AND APPARATUS FOR PREVENTING ATRIAL FUSION DURING AUTOMATIC PACING THRESHOLD DETERMINATION IN A CARDIAC STIMULATION DEVICE

(75) Inventor: Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 198 days.

(21) Appl. No.: 09/970,192

(22) Filed: Oct. 2, 2001

Related U.S. Application Data

(63) Continuation of application No. 09/488,731, filed on Jan. 20, 2000, now Pat. No. 6,339,723.

(51) Int. Cl.$^7$ ............ A61N 1/362; A61N 1/37
(52) U.S. Cl. ............................................... 607/28
(58) Field of Search .................. 607/9, 14, 27, 607/28

(56) References Cited

U.S. PATENT DOCUMENTS

| | | | |
|---|---|---|---|
| 3,949,758 A | 4/1976 | Jirak | 128/419 |
| 4,686,988 A | 8/1987 | Sholder | 128/419 |
| 5,766,229 A | 6/1998 | Bornzin | 607/28 |
| 6,339,723 B1 * | 1/2002 | Sloman | 607/28 |

* cited by examiner

Primary Examiner—Jeffrey R. Jastrzab

(57) ABSTRACT

An implantable cardiac stimulation device is provided which alters the stimulation regime during determination of a capture threshold level. In order to avoid the potential for fusion beats which would interfere with a capture threshold level determination, a two-fold approach is used. First, the atrial refractoriness of the atrium of the patient's heart is extended by supplying a secondary atrial stimulation pulse during a prescribed time period following delivery of a primary atrial stimulation pulse. Second, the atrium is overdriven by providing an atrial stimulation pulse at a rate in excess of the intrinsic heart rate. Accordingly, the potential for fusion beats is significantly decreased and the reliability of the determined capture threshold level is increased. In a preferred embodiment, two closely placed stimulation pulses, i.e., a first primary atrial stimulation pulse and a secondary atrial stimulation pulse, are provided to an atrium of the patient's heart, and a second primary atrial stimulation pulse set to a test level is delivered faster than the heart's intrinsic rate. During this pacing regime, the potential for fusion beats is decreased and accordingly, sensing the presence or absence of evoked responses can accurately determine the capture threshold level.

25 Claims, 4 Drawing Sheets

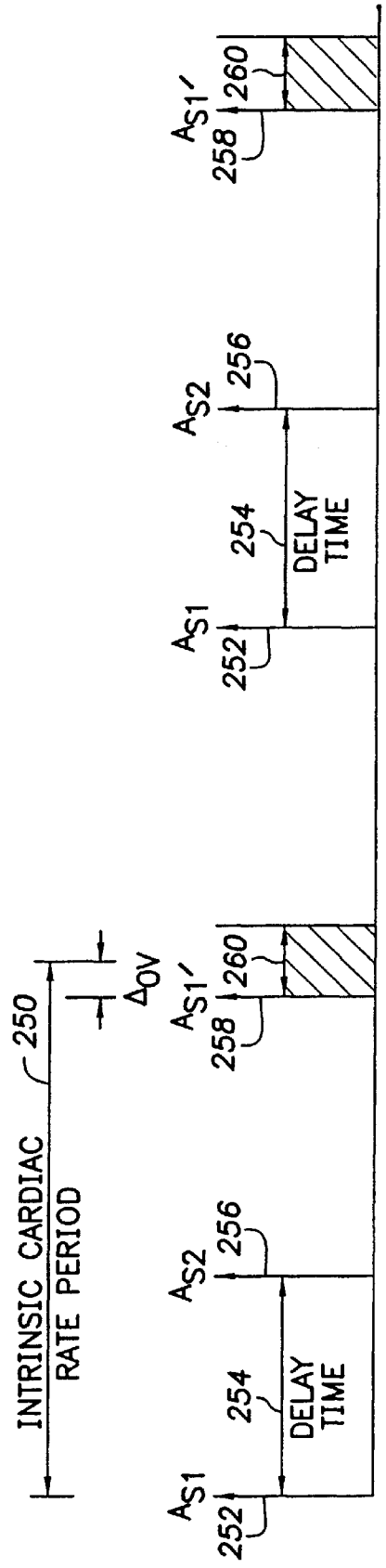
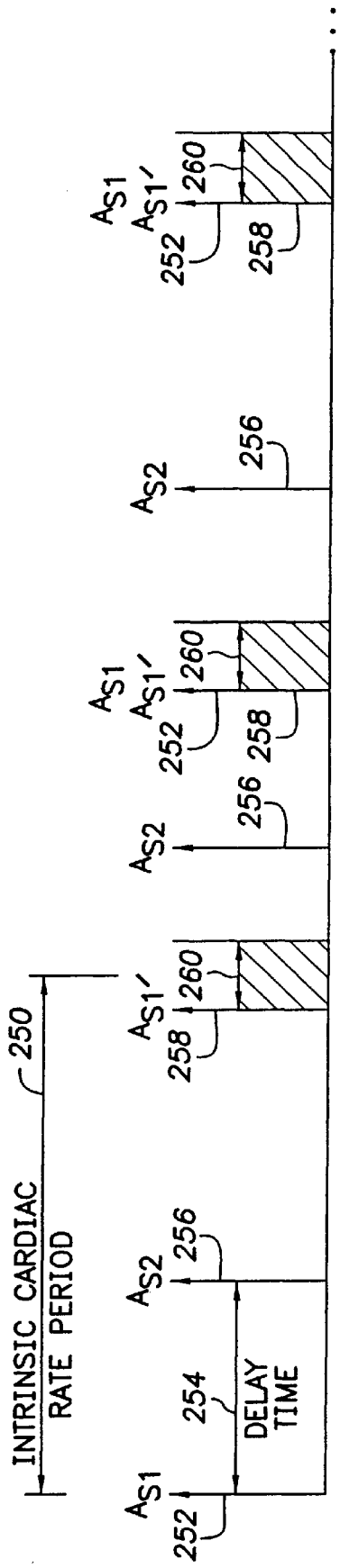
FIG. 4A
FIG. 4B

METHOD AND APPARATUS FOR PREVENTING ATRIAL FUSION DURING AUTOMATIC PACING THRESHOLD DETERMINATION IN A CARDIAC STIMULATION DEVICE

CROSS-REFERENCE TO RELATED APPLICATIONS

The application is a continuation of U.S. patent application Ser. No. 09/488,731, filed Jan. 20, 2000 now U.S. Pat. No. 6,339,723.

FIELD OF THE INVENTION

The present invention generally relates to implantable medical devices and more particularly to cardiac stimulation devices, e.g., pacemakers, ICDs and the like, using fusion avoidance methods to improve the performance of automatic threshold determination techniques which are employed by such devices.

BACKGROUND OF THE INVENTION

Implantable pacemakers generate electrical stimulation pulses and deliver such stimulation pulses to atrial and/or ventricular muscle tissue of a patient's heart at a prescribed rate and/or rhythm when, through disease or other causes, the heart is not able to maintain the prescribed heart rate or rhythm on its own. When the delivered electrical stimuli are of sufficient energy, they cause the cardiac muscle tissue to depolarize, and therefore contract, thereby forcing the heart rate or rhythm to track the delivery of the electrical stimuli. When the delivered electrical stimuli are of insufficient energy, depolarization does not occur, and the heart rate or rhythm is not controlled by the pacemaker. Hence, for the pacemaker to perform its intended function, it is critically important that the delivered electrical stimuli be of sufficient energy to depolarize the cardiac tissue, a condition known as "capture".

The energy of the electrical stimuli generated by an implanted pacemaker is derived from the energy stored in the pacemaker's battery. The pacemaker's battery has a limited amount of energy stored therein, and the generation of electrical stimuli represents by far the greatest drain of such energy. In order to preserve this limited energy and prolong the life of the battery, it is known in the art to adjust the energy of the delivered electrical stimuli, generally the amplitude of the stimulation voltage, so that it is just sufficient to cause capture, with an appropriate safety margin. See, e.g., U.S. Pat. Nos. 3,949,758 and 4,686,988. The amount of energy needed to effectuate capture is known as the capture "threshold", and electrical stimuli of energy less than the capture threshold do not bring about capture, while electrical stimuli of energy greater than the capture threshold do bring about capture. By adjusting the energy of the electrical stimuli so that it is always greater than the capture threshold, but not too much greater, the limited energy of the pacemaker battery may thus be preserved. The battery energy is preserved because: (1) electrical stimuli of insufficient energy to cause capture (electrical stimuli below threshold), which stimuli represent wasted energy, are rarely generated; and (2) electrical stimuli of excessive energy (energy much greater than the capture threshold), which excess energy not only represents wasted energy, but also energy that may disadvantageously cause pectoral stimulation and/or sensation, are also rarely generated.

In order to determine the capture threshold, prior art devices periodically enter into an autothreshold determination mode in which a stimulation pulse is delivered and the electrical signals from the cardiac tissue are monitored to determine if depolarization has occurred. Generally, autothreshold determinations decrease the amplitude of a stimulation pulse (from an initial maximum value) until capture is lost and then use this loss of capture amplitude value plus a safety margin value as the new capture threshold value. However, this procedure assumes that the cardiac signals only represent evoked responses to the stimulation pulses, e.g., intrinsic P-waves are not present. However, in certain cases referred to as fusion, intrinsic P-waves may coincide with the stimulation pulses and thus both events contribute to the sensed electrical activity of the cardiac tissue. Accordingly in such cases, an autothreshold determination could be unreliable since the intrinsic event may mask the evoked response. U.S. Pat. No. 5,766,229 to Bornzin, whose teachings are incorporated herein by reference, teaches that fusion must be prevented in order to provide a reliable atrial autothreshold determination. In the Bornzin patent, fusion is prevented by overdriving the atrial pacing rate based upon a variance of the intrinsic rate. While this technique reduces the probability of a fusion beat, it is believed that this technique will not eliminate fusion. Accordingly, what is needed is a method for providing an additional level of certainty that fusion beats will not interfere with the autothreshold determination process.

SUMMARY OF THE INVENTION

The present invention is directed to an implantable cardiac stimulation device, e.g., a pacemaker, ICD or the like, and associated method for altering the stimulation regime during determination of a capture threshold level. In order to avoid the potential for fusion beats which would interfere with a capture threshold level determination, a two-fold approach is used. First, the atrial refractoriness of the atrium of the patient's heart is extended by supplying a secondary atrial stimulation pulse during a determined time period following delivery of a primary atrial stimulation pulse. Second, the atrium is overdriven by providing an atrial stimulation pulse at a rate in excess of the intrinsic heart rate. Accordingly, the potential for fusion beats is significantly decreased and the reliability of the determined capture threshold level is increased. In a preferred embodiment, two closely placed stimulation pulses, i.e., a first primary atrial stimulation pulse and a secondary atrial stimulation pulse, are provided to an atrium of the patient's heart and a second primary atrial stimulation pulse set to a test level is delivered faster than the heart's intrinsic rate. During this pacing regime, the potential for fusion beats is decreased and accordingly, sensing the presence or absence of evoked responses can accurately determine the capture threshold level.

A preferred method for suppressing fusion beats to thereby facilitate the periodic determination of a capture threshold level for pacing the atrium of a patient's heart comprises (1) determining the intrinsic cardiac rate, (2) delivering a first primary atrial stimulation pulse having a first amplitude level to an atrium of the patient's heart, (3) timing a delay time period following the primary atrial stimulation pulse, (4) delivering a secondary atrial pacing pulse having a second amplitude level to the atrium of the patient's heart at the end of the delay time period, and (4) delivering a second primary atrial stimulation pulse having a third amplitude level to the atrium of the patient's heart, whereby the second primary atrial stimulation pulse is delayed from the first primary atrial stimulation pulse by a time period defining a cardiac rate in excess of the intrinsic cardiac rate, whereby the likelihood of fusion beats is minimized.

In a further aspect of a preferred embodiment, the first primary atrial stimulation pulse and the secondary atrial stimulation pulse are both configured to have high amplitudes, selected to ensure capture of the atrium of the patient's heart. In an alternative embodiment, the first primary atrial pulse may be set to an amplitude corresponding to the second primary atrial stimulation pulse which is set to the test level during the capture threshold determination.

The capture threshold determination may run continuously until completed or one determination portion may be done at a time. Specifically, the two fast pulses, i.e., the first primary atrial stimulation pulse and the secondary atrial stimulation pulse, will precede each second primary atrial stimulation pulse which is used to determine capture. However, in a first embodiment, the next second primary atrial stimulation pulse (used to determine capture) will not occur until two more fast pulses are delivered. Alternatively, the second primary atrial stimulation pulse can serve multiple functions. First, it is used to determine capture. Second, it is used as the next first primary atrial stimulation pulse and is directly followed in the same cardiac cycle by a secondary atrial stimulation pulse, i.e., it also becomes one of the two fast pulses for the next second primary atrial stimulation pulse.

The novel features of the invention are set forth with particularity in the appended claims. The invention will be best understood from the following description when read in conjunction with the accompanying drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference characters identify identical elements, and wherein:

FIGS. 4A and 4B are timing diagrams of the sequence of stimulation pulses generated by the embodiments described in reference to FIG. 3.

DETAILED DESCRIPTION OF THE PREFERRED EMBODIMENTS

The present invention is directed to an implantable cardiac stimulation device, e.g., a pacemaker, ICD or the like, and associated method for altering the stimulation regime during determination of a capture threshold level. In order to avoid the potential for fusion beats which would interfere with a capture threshold level determination, a two-fold approach is used. First, the atrial refractoriness of the atrium of the patient's heart is extended by supplying a secondary atrial stimulation pulse during a determined time period following delivery of a primary atrial stimulation pulse. Second, the atrium is overdriven by providing an atrial stimulation pulse at a rate in excess of the intrinsic heart rate. Accordingly, the potential for fusion beats is significantly decreased and the reliability of the determined capture threshold level is increased. In a preferred embodiment, two otherwise unrelated techniques are combined. In a first technique, two closely placed stimulation pulses, i.e., a first primary atrial stimulation pulse and a secondary atrial stimulation pulse, are provided to an atrium of the patient's heart. Such a technique, as taught in a copending, commonly-owned application entitled "Implantable Pacemaker and Method for Prolonging Atrial Refractoriness" by Bornzin et al., tends to extend the refractory period for the atrium and thus slow down the atrial rate. Additionally, this technique will tend to reduce the probability of fusion due to the slowed down atrial rate. The Bornzin et al. application is incorporated herein by reference in its entirety. In a second technique, taught in U.S. Pat. No. 5,766,229 to Bornzin et al., fusion beats can be avoided by overdriving the atrium, i.e., by pacing the atrium at a rate exceeding its intrinsic rate. The Bornzin '229 patent is incorporated by reference herein in its entirety. By combining these techniques during an autothreshold determination, the potential for fusion beats is decreased and accordingly, sensing the presence or absence of evoked responses can accurately determine the capture threshold level.

Figure 1:
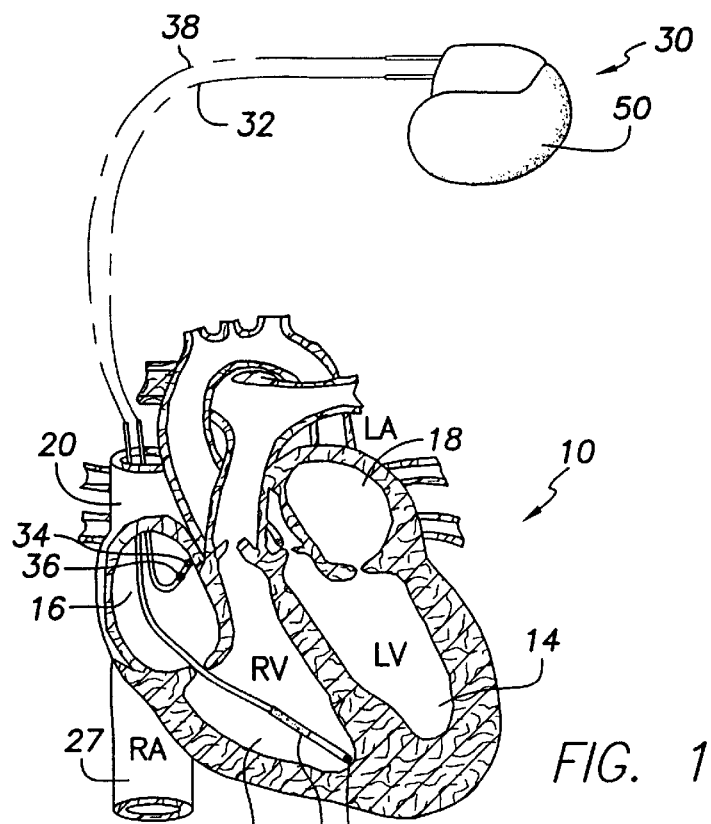
FIG. 1 is a schematic illustration of a human heart, in need of cardiac rhythm management, shown in association with an implantable pacemaker embodying the present invention.

Referring now to FIG. 1, a heart 10 in need of cardiac rhythm management and an associated implantable pacemaker 30 embodying the present invention are shown. The portions of the heart 10 illustrated in FIG. 1 are the right ventricle 12, the left ventricle 14, the right atrium 16 and the left atrium 18. Also illustrated are the superior vena cava 20 and inferior vena cava 27. As is well known in the art, the pacemaker 30 is arranged to be implanted in an upper left chest portion of a patient within a subcutaneous pocket.

The pacemaker 30 includes a first endocardial lead 32 preferably having an electrode pair including a distal electrode 34 and a proximal electrode 36 implanted in electrical contact with an atrium of the patient's heart. The electrodes 34 and 36 are implanted in the right atrium 16 to support sensing of right atrial electrical activity and delivery of pacing pulses to the right atrium 16.

Similarly, a second endocardial lead 38 preferably has an electrode pair including a distal electrode 40 and a proximal electrode 42 implanted in electrical contact with a ventricle of the patient's heart. The electrodes 40 and 42 are implanted in the right ventricle 12 to support sensing of right ventricular electrical activity and delivery of pacing pulses to the right ventricle 12.

Figure 2:
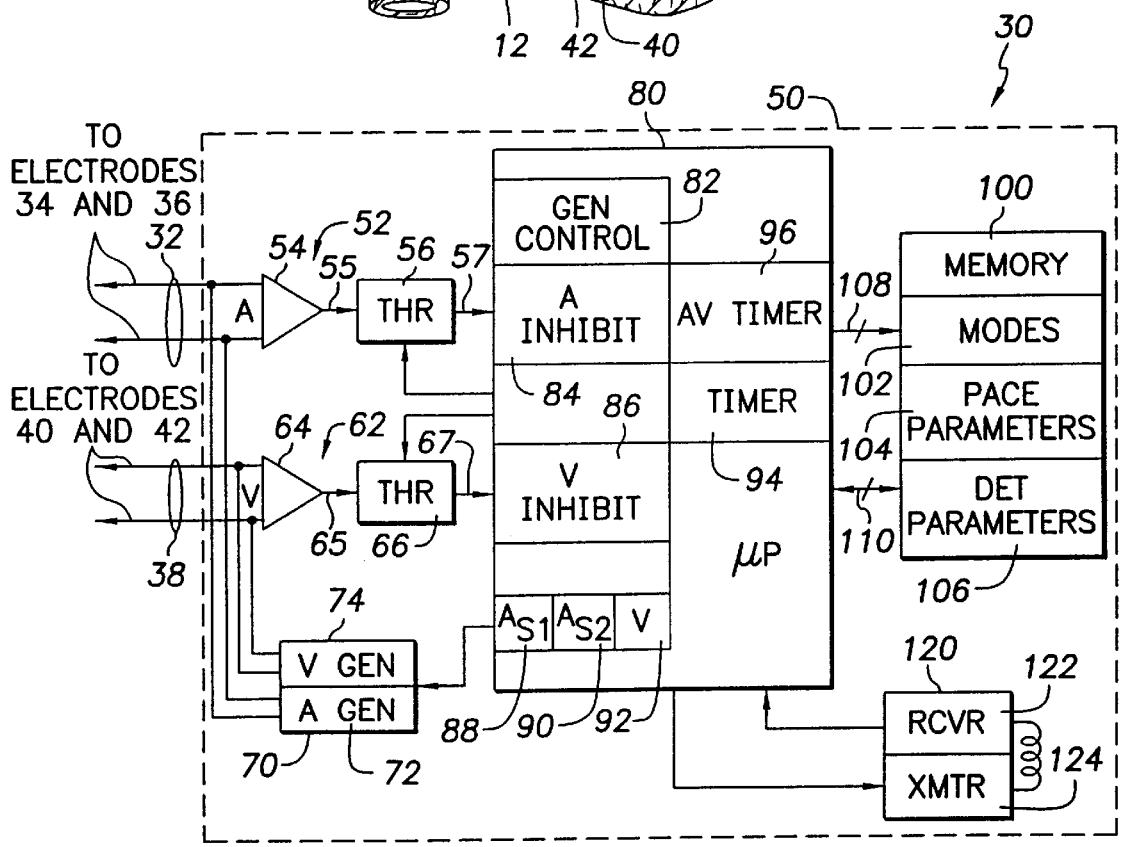
FIG. 2 is a block diagram of the implantable pacemaker of FIG. 1.

The implantable pacemaker 30 includes a hermetically sealed, electrically conductive enclosure 50. As illustrated in FIG. 2, the pacemaker 30 includes within the enclosure 50 an atrial sense channel 52, a ventricular sense channel 62, and a pacing pulse generator 70 including a first or atrial pulse generator 72 (A Gen) for providing atrial pacing pulses and a second or ventricular pulse generator 74 (V Gen) for providing ventricular pacing pulses. The pacemaker 30 further includes a control circuit 80, preferably a microprocessor, a memory 100 and a telemetry stage 120.

The atrial sense channel 52 includes an atrial sense amplifier 54 and an atrial threshold detector 56. The atrial sense amplifier 54 has inputs coupled to electrodes 34 and 36 of lead 32 and generates an output signal 55 which is input to the atrial threshold detector 56. As further illustrated the atrial threshold detector 56 has an output 57 which is coupled to the microprocessor 80.

The atrial sense amplifier 54, together with electrodes 34 and 36 sense electrical activity in the right atrium 16. When the output 55 from the atrial sense amplifier 54 transitions through a programmed threshold of the atrial threshold detector 56, the atrial threshold detector 56 provides input signal 57 to the microprocessor 80 indicating that an atrial activation or P-wave has been detected. Such detection is well known in the art.

Similarly, the ventricular sense channel 62 includes a ventricular sense amplifier 64 and a ventricular threshold detector 66. The ventricular sense amplifier 64 has inputs coupled to the electrodes 40 and 42 of lead 38 and generates an output signal 65 which is input to the ventricular threshold detector 66. As further illustrated, the ventricular threshold detector 66 has an output 67 which is coupled to the microprocessor 80.

The ventricular sense amplifier 64, together with electrodes 40 and 42 sense electrical activity in the right ventricle 12. When the output 65 of the ventricular sense amplifier 64 transitions through a programmed threshold of the ventricular threshold detector 66, the ventricular threshold detector 66 provides an input signal 67 to the microprocessor 80 indicating that a ventricular activation or R-wave has been detected. Such detection is also well known in the art.

The first, or atrial pulse generator 72 has outputs coupled to electrodes 34 and 36 through lead 32. This permits pacing pulses produced by the atrial pulse generator 72 to be applied to the right atrium 16. As will be seen hereinafter, these pacing pulses include primary atrial pacing stimulation pulses ($A_{s1}$ and $A_{s1}'$) and secondary atrial pacing stimulation pulses ($A_{S2}$).

The second or ventricular pulse generator 74 has outputs coupled to electrodes 40 and 42 through lead 38. This permits pacing pulses produced by the ventricular pulse generator 74 to be applied to the right ventricle 12.

The sense channels 52 and 62 and pulse generators 72 and 74 permit the pacemaker 30, in accordance with the present invention, to provide single chamber atrial pacing or combined dual chamber atrial and ventricular pacing. The overall functioning of the pacemaker 30 is controlled by the microprocessor 80.

The microprocessor 80 implements selected pacing modalities by executing operating instructions stored in the memory 100, and more specifically, in a memory portion 102. In executing the instructions stored in memory portion 102, the microprocessor 80 further utilizes pacing parameters stored in memory portion 104 and detection parameters stored in memory portion 106. The pacing parameters may include, for example, AV delays, atrial and ventricular pacing energies, atrial and ventricular escape intervals, and basic rates, etc. The detection parameters may include, for example, blanking period durations, refractory periods, and detection thresholds for the threshold detectors 56 and 66. Such pacing parameters and detection parameters are well known in the art.

The telemetry stage 120 permits mode selections and storage of pacing and detection parameters in the memory 100 to be made through the use of an external programmer (not shown) of the type well known in the art. The telemetry stage includes a receiver 122 which receives telemetry commands including mode selection commands and pacing and detection parameters from the programmer. The receiver 122 conveys the commands to the microprocessor 80 which then stores them in memory 100.

The telemetry stage 120 also includes a transmitter 124. The transmitter may be used for transmitting data to the programmer. The transmitted data may include sensed electrograms or status information, for example, as is well known in the art.

The microprocessor 80 is coupled to the memory 100 by a multiple-bit address bus 108 and a bi-directional, multiple-bit data bus 110. The microprocessor 80 uses the address bus 108 to fetch operating instructions or programmable parameters from the memory at address locations defined on the address bus 108. The fetched instructions and parameters are conveyed to the microprocessor 80 over the data bus 110. Similarly, the microprocessor 80 may store data in the memory 100 at memory locations defined on the address bus 108. The microprocessor 80 conveys the data to the memory over the data bus 110. Such microprocessor and memory operations are conventional in the art.

When executing the operating instructions stored in memory 100, the microprocessor 80 implements a number of functional stages in accordance with the present invention. Those stages include a generator control stage 82 which includes an atrial generator inhibiting stage 84, a ventricular generator inhibiting stage 86, a primary atrial pacing pulse stimulation control 88 ($A_{S1}$), a secondary atrial pacing pulse stimulation control 90 ($A_{S2}$), and a ventricular pacing pulse stimulation control 92 (V). The stages of microprocessor 80 further include an atrial delay timer 94 and an AV delay timer 96.

In accordance with a primary aspect of the present invention, whether the pacemaker 30 is in a single or dual chamber pacing modality, the generator control stage 82 causes the atrial pulse generator 72 to provide a secondary atrial pacing pulse to the right atrium 16 a secondary pacing pulse delay time after causing the atrial pulse generator 72 to provide a primary atrial pacing pulse to the right atrium 16. When atrial pacing is in a demand mode, the generator control stage 82 inhibits the atrial pulse generator 72, and thus the delivery of the primary pacing pulse if an atrial event, i.e., depolarization signifying activation of the atrium, is detected during an atrial escape interval. However, the generator control stage 82 still causes the atrial pulse generator 72 to deliver the secondary atrial pacing pulse after the secondary pacing pulse delay time following detection of the atrial event. The secondary atrial pacing pulse prolongs the refractoriness of the atria. The secondary pacing pulse delay time period, i.e., the period of time between the primary atrial pacing pulse or the detected atrial depolarization and the secondary atrial pacing pulse, is preferably between about 180 to 300 milliseconds. The atrial refractory period is typically about 130 milliseconds in normal patients but may be as short as 80 milliseconds in some patients with recurrent atrial arrhythmias. Accordingly, the secondary pacing pulse will serve to prolong the period during which the atria are refractory and thus decrease the likelihood of a spontaneous reentrant arrhythmia. The ventricle and the AV node will be refractory when the secondary atrial pacing pulse is delivered. As a result, the secondary atrial pulse will have no affect on the ventricle. Atrial kick will be provided by the primary depolarization and it is likely that the atria will be in hemodynamic block. Thus, the hemodynamics will not be disturbed by the secondary atrial pacing pulse.

As previously mentioned, the atrial pacing may be in a demand mode. To that end, the atrial generator inhibiting stage 84 preferably includes an atrial delay timer 94 for timing an atrial escape interval. If, during the atrial escape interval, the atrial sense channel 52 detects an atrial event, the atrial generator inhibiting stage 84 will preclude the primary atrial pulse stimulation control 88 from issuing a control signal to the atrial pulse generator 72 and thus will inhibit delivery of the primary pacing pulse. However, upon detection of an atrial event by the atrial sense channel 52, the atrial delay timer 94 begins timing the secondary pacing pulse delay period. At the end of the secondary pacing pulse delay time period, the secondary atrial pacing pulse stimulation control 90 issues a control signal to the atrial pulse generator 72 to cause it to provide the secondary atrial pacing pulse.

If an atrial event is not detected by the atrial sense channel 52 during the atrial escape interval, the primary atrial pacing pulse stimulation control 88 issues a control signal to the atrial pulse generator 72 at the end of the atrial escape interval to cause it to provide the primary atrial pacing pulse. When the primary atrial pacing pulse is provided by atrial pulse generator 72, the atrial delay timer 94 commences to time the secondary pacing pulse delay time period. At the end of the secondary pacing pulse delay time, the secondary atrial pacing pulse stimulation control 90 then issues a control signal to the atrial pulse generator 72 to cause the generator 72 to provide the secondary atrial pacing pulse.

The atrial pacing described above may be provided in a single chamber atrial pacing modality. In such a modality, the primary pacing pulses, absent spontaneous atrial activations, will occur at a basic rate consistent with a basic pacing rate stored in memory portion 104 of memory 100. However, the atrial pacing may be provided in association with ventricular pacing as well.

When dual chamber pacing is provided, the provision of a primary atrial pacing pulse or the detection of an atrial activation during the atrial escape interval causes the AV delay timer 96 to time an AV delay time period. At the end of the AV delay time period, the ventricular pacing pulse stimulation control 92 issues a control signal to the ventricular pulse generator 74 causing it to provide a ventricular pacing pulse to the right ventricle 12. Additionally, the ventricular pacing may further be in a demand mode. To that end, if a ventricular activation is detected by the ventricular sense channel 62 during the AV delay time period timed by the AV delay timer 96, the ventricular inhibit stage 86 will preclude the ventricular pacing pulse stimulation control 92 from issuing its control signal to the ventricular generator 74 and thus inhibiting the delivery of the ventricular pacing pulse.

In view of the foregoing, it may be seen that in a first portion of the present invention, an implantable cardiac stimulation device is shown which extends the atrial refractory period of a patient's heart. The secondary atrial pacing pulse follows a primary atrial pacing pulse by a predetermined time period, typically between 180 to 300 milliseconds. This timing will not disturb the hemodynamics of the heart and the second atrial stimulus will not be conducted because the ventricle and AV node will be refractory due to a conducted ventricular depolarization or because of a paced ventricular depolarization. Additionally, the secondary atrial pacing pulse may slow the sinus rate of the heart, thus increasing the likelihood of dynamic atrial overdrive pacing wherein overdriving the intrinsic atrial rhythm may occur. Accordingly in a second portion of the present invention, the primary atrial stimulation pulse (actually the second primary atrial stimulation pulse) is overdriven to further suppress the potential for a fusion beat. To overdrive the atrial rate, the intrinsic cardiac rate time period is first determined, either by sensing the time period between intrinsic atrial beats or ventricular beats, and the time period is shortened in determining when to provide the second primary atrial stimulation pulse. Accordingly, the atrial stimulation pulse will precede and thus suppress any intrinsic P-wave.

Figure 3:
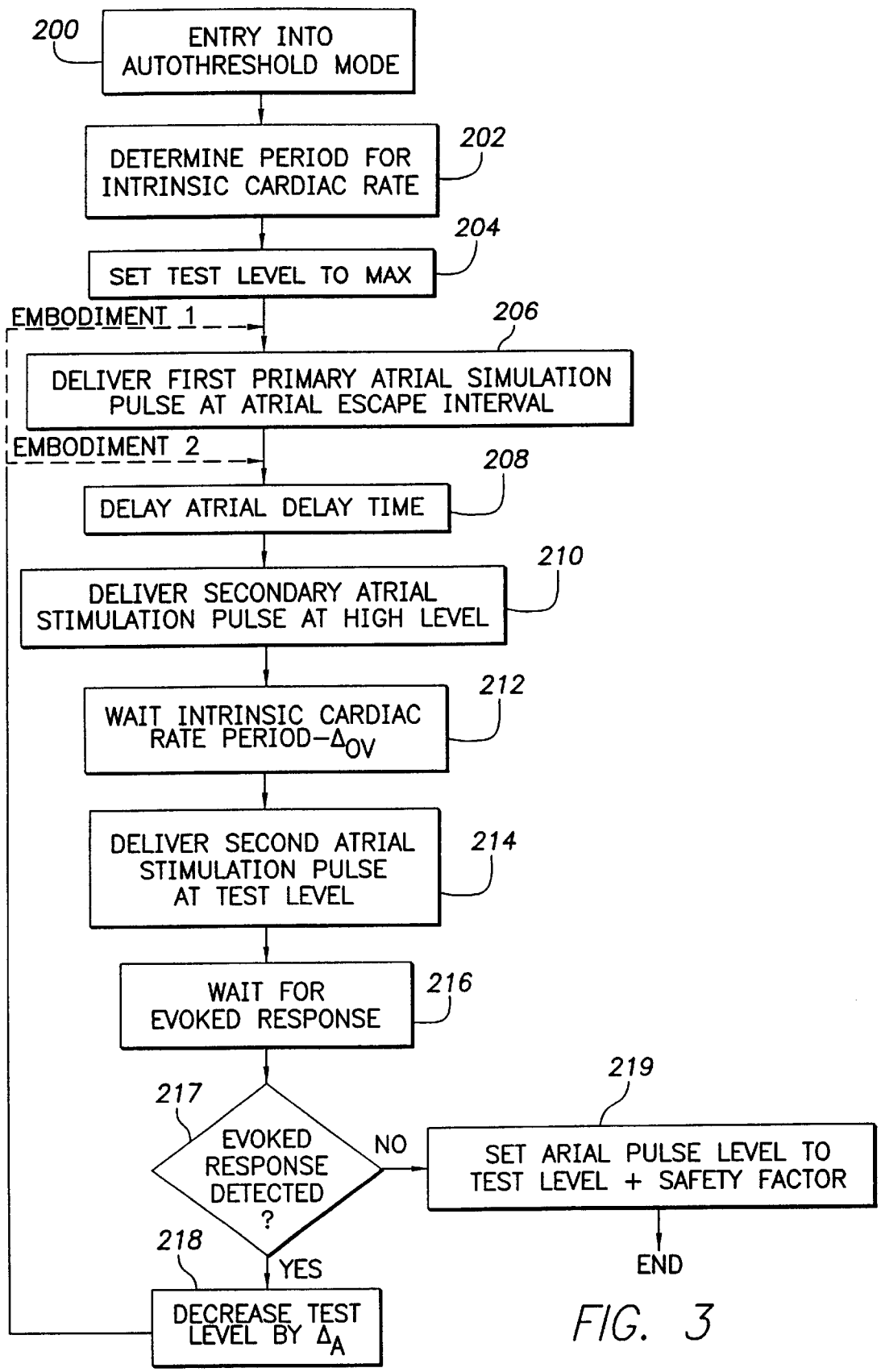
FIG. 3 is a simplified flowchart of an exemplary implementation of the method of the present invention.

FIG. 3 shows an exemplary flow chart of the process of the present invention. FIGS. 4A and 4B show simplified timing diagrams corresponding to the flow chart of FIG. 3. Periodically, the process determines in step 200 that the criteria have been satisfied for entering into an autothreshold determination. Typically, this determination is made periodically, e.g., once or twice a day, or upon occurrence of an event, e.g., loss of capture. In step 202, the time period for the intrinsic cardiac rate is determined. The time period is measured by determining the time elapsed between two common types of cardiac events 250, e.g., two atrial events using the atrial sense channel 52 or two ventricular events using the ventricular sense channel 62. In step 204, a test level used for the autothreshold test is initially set to a maximum value, e.g., 4.5 volts. In step 206, following an atrial escape interval, the first primary atrial stimulation pulse ($A_{S1}$) 252 is delivered to the atrium of the patient's heart at the beginning of a cardiac cycle. In a preferred embodiment, stimulation pulse 252 is preferably set to a high output level, e.g., 4.5 volts, a value that will capture the patient's heart. In step 208, a determined atrial delay time 254 is passed. The atrial delay time may be set to a predetermined value, e.g., between 180 to 300 ms, or may be automatically determined as described below in reference to FIG. 5. Following step 208, the secondary atrial stimulation pulse ($A_{S2}$) 256 is delivered at a high output voltage level, e.g., 4.5 volts, in step 210. The secondary atrial stimulation pulse 256 is delivered shortly after the first primary atrial stimulation pulse 252 (separated by the atrial delay time 254 processed in step 208). Accordingly, these are referred to as two fast pulses. As previously discussed, these fast pulses serve to extend the refractory period of the atrium and thus slow down the atrium and helps to reduce the possibility of a fusion beat. The second primary atrial stimulation pulse 258 is delivered at the beginning of the next cardiac cycle in step 214. However, to further minimize the potential for a fusion beat, the second primary atrial stimulation pulse ($A_{S1}'$) 258 is delivered sooner by an overdrive value $\Delta_{OV}$, e.g., 50 ms., than the determined intrinsic cardiac rate period 250 determined in step 202 as processed in step 212. Accordingly, the atrium is overdriven. Now, with the potential for a fusion beat significantly minimized, an autothreshold determination can be made in the following steps. In step 216, the process waits for a predetermined period 260, e.g., 60 ms., for an evoked response to the second primary stimulation pulse 258. If an evoked response is detected during window 260 in step 217, the test level is still above the capture threshold. Accordingly, the test level is decrease by a predetermined amount $\Delta_A$, e.g., 0.250 volts, and the process continues. In a first embodiment (as shown in FIG. 4A), the process continues at step 206 where the next atrial pulse delivered is a first primary atrial stimulation pulse ($A_{S1}$) 256. Alternatively, the process may continue with step 208 and a secondary atrial stimulation pulse is delivered after the atrial delay time 254. In this embodiment, the second primary atrial stimulation pulse 258 for one test cycle also becomes the first primary atrial stimulation pulse 252 for the next test cycle. This embodiment may offer some advantages since the capture threshold can be determined faster and with the use of less energy since it is already known that second primary atrial stimulation pulse ($A_{S1}'$) 258 was captured (or else the process would have already terminated). If, in step 219, capture was lost, the capture threshold level is set to the current test level plus a safety factor, e.g., a percentage or a predetermined voltage level, e.g., 0.250 volts) and the autothreshold process completes.

As has been discussed, the atrial refractory period can be extended by providing a secondary atrial pulse a delay time following the delivery of a primary atrial pulse. However, the delay time must be within an appropriate range for each patient. If the delay time is too short, e.g., less than 120 to 150 ms., the secondary atrial pulse may cause atrial fibrillation. If the delay time is too long, e.g., greater than 300 ms., the AV node will no longer be in its refractory period and the ventricle may be stimulated. Accordingly, an exemplary auto-adjustment mode for determining optimal AA (primary atrial pulse to secondary atrial pulse) and PA (intrinsic P-wave to secondary atrial pulse) delay time values, is presented in reference to FIG. 5.

Figure 5:
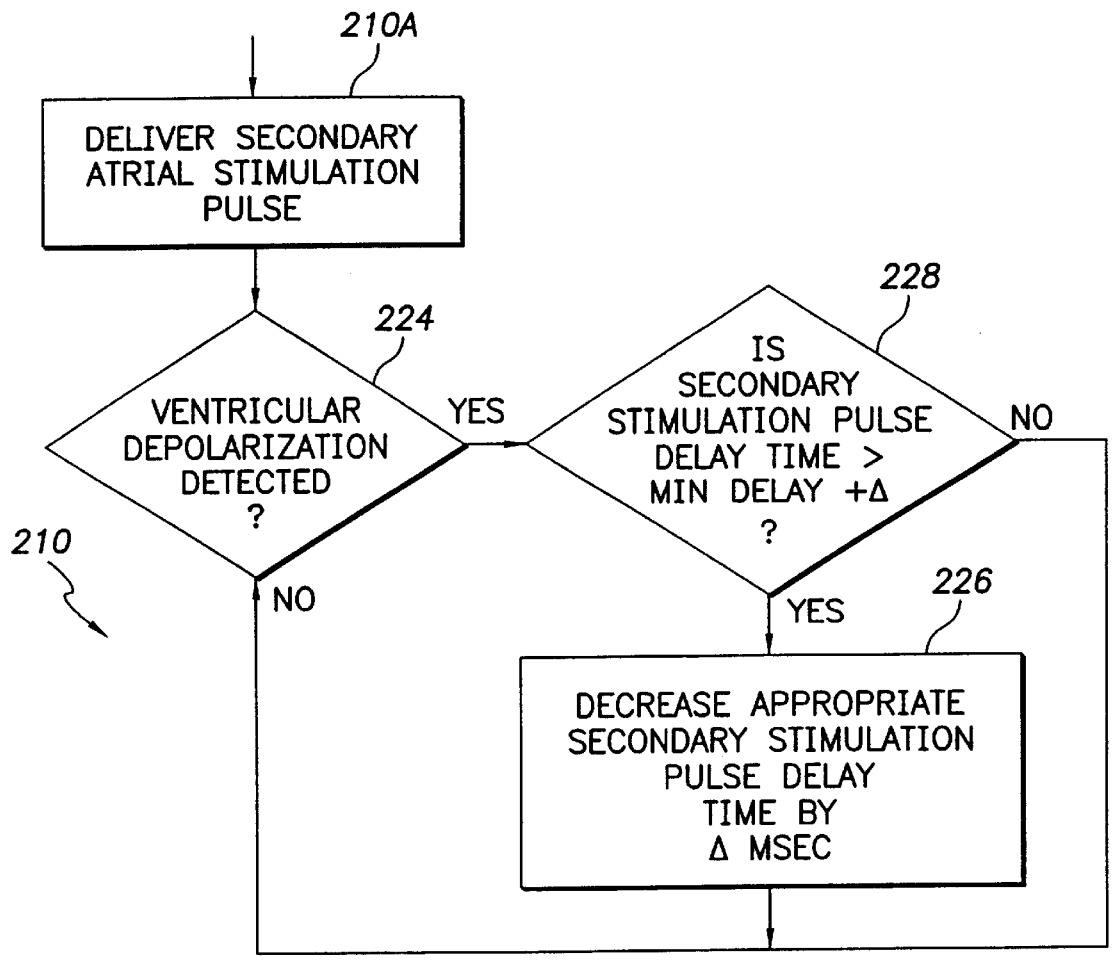
FIG. 5 is a simplified flowchart of an exemplary process for automatically adjusting the atrial delay time between a primary atrial event and delivery of the secondary atrial pacing pulse if a ventricular depolarization occurs in response to the secondary atrial pacing pulse.

Following, a predetermined time period (see step 220), e.g., once an hour to once a day, the M and PA delay time values are extended to a MaxDelay value, e.g., 350 ms., (see step 222) to restart an auto-adjustment process. These delay time values are used in step 210 (see FIG. 3 to determine when the secondary atrial pulse should be delivered. However, as shown in FIG. 5 optimal delay time values are determined. Following the delivery of the secondary atrial pulse in step 210A, the microprocessor 80 determines in step 224 using the ventricular sense channel 62 whether a ventricular activation, i.e., depolarization occurred. If ventricular depolarization occurs, then the appropriate delay time value is decreased in step 226 by a predetermined amount Δ, e.g., 5 ms. The appropriate delay time value is selected by determining by whether the primary atrial event was either the delivery of a primary atrial pulse (in which case the AA delay time is decreased) or whether the primary atrial event was the detection of a P-wave (in which case the PA delay time is decreased). However, as previously discussed, the delay time values are not allowed to decrease below a MinDelay time, e.g., 120 to 150 ms. Accordingly, it is determined in step 228 whether current delay time value +Δ exceeds the MinDelay value. If this condition is not satisfied, step 226 is bypassed.

While the invention has been described by means of specific embodiments and applications thereof, it is understood that numerous modifications and variations could be made thereto by those skilled in the art without departing from the spirit and scope of the invention. For example, while the prior description has been primarily directed to an embodiment of the present invention that uses a pacemaker for atrial pacing according to the described pacing regime, other cardiac stimulation devices, e.g., ICDs and those that employ dual site or ventricular pacing are also considered to be within the scope of the present invention. For example, dual site atrial pacing may be provided by a second atrial electrode pair being implanted in the coronary sinus near the left ventricular free wall or, during open heart surgery, being placed on the left atrial myocardium. The second atrial electrode pair may then be paced simultaneously with the atrial electrode pair implanted in the right atrium. It is therefore to be understood that within the scope of the claims, the invention may be practiced otherwise than as specifically described herein.

What is claimed is:

1. An implantable cardiac stimulation device for stimulating a patient's heart through a first electrode adapted for electrical contact with an atrium of the patient's heart, the implantable cardiac stimulation device comprising:
   a pulse generator adapted to be electrically coupled to the first electrode and configured to generate atrial stimulation pulses at a programmed amplitude level and rate for stimulating the patient's heart;
   an atrial detection circuit, adapted to be electrically coupled to the first electrode, configured to detect a presence or an absence of an evoked response to a stimulation pulse from the pulse generator, wherein the detected absence of an evoked response indicates a potential occurrence of a fusion beat; and
   a controller, coupled to the pulse generator and the atrial detection circuit, configured to determine a capture threshold level in response to the absence of an evoked response, wherein the controller causes the pulse generator to deliver a first atrial stimulation pulse at a first amplitude level and a second atrial stimulation pulse at a second amplitude level an atrial delay time after the first atrial stimulation pulse, whereby the second atrial stimulation pulse minimizes a potential occurrence of subsequent fusion beats by prolonging atrial refractoriness.

2. The implantable cardiac stimulation device of claim 1, wherein the first amplitude level of the first atrial stimulation pulse is a predetermined high level selected to ensure stimulation of the atrium of the patient's heart.

3. The implantable cardiac stimulation device of claim 1, wherein the second amplitude level of the second atrial stimulation pulse is a predetermined high level selected to ensure stimulation of the atrium of the patient's heart.

4. The implantable cardiac stimulation device of claim 1, wherein the determined atrial delay time is between about 180 milliseconds and 300 milliseconds.

5. The implantable cardiac stimulation device of claim 1, wherein the controller further causes the pulse generator to generate a test stimulation pulse at a third amplitude level delayed by a time period defining a cardiac rate in excess of the patient's intrinsic cardiac rate, whereby the potential occurrence of subsequent fusion beats is further minimized.

6. The implantable cardiac stimulation device of claim 5, wherein the third amplitude level of test stimulation pulse is a programmable test level, and wherein the atrial detection circuit determines the presence of an evoked response to the test stimulation pulse.

7. The implantable cardiac stimulation device of claim 5, wherein the first amplitude level of first atrial stimulation pulse is a programmable test level corresponding to the third amplitude level of the test stimulation pulse.

8. The implantable cardiac stimulation device of claim 5, wherein the intrinsic cardiac rate is periodically determined using the atrial detection circuit by measuring the time period between successive P-waves.

9. The implantable cardiac stimulation device of claim 5, further comprising:
   a ventricular detection circuit adapted to be electrically coupled to a second electrode adapted for electrical contact with a ventricle of the patient's heart; and
   wherein the intrinsic cardiac rate is periodically determined using the ventricular detection circuit by measuring the time period between successive R-waves.

10. The implantable cardiac stimulation device of claim 5, wherein the controller is configured to cause the pulse generator to deliver at least one stimulation pulse at a predetermined amplitude level to cause capture of the heart following each test stimulation pulse to prolong atrial refractoriness.

11. The implantable cardiac stimulation device of claim 5, wherein the controller is configured to determine a capture threshold level for stimulating the patient's heart, and wherein the controller decreases the third amplitude level in subsequent test atrial stimulation pulses in response to the presence of a corresponding evoked response to each test stimulation pulse, and sets the capture threshold level to the third amplitude level plus a safety margin in response to the absence of an evoked response to a test stimulation pulse.

12. The implantable cardiac stimulation device of claim 5, further comprising an atrial delay timer for timing the atrial delay time.

13. The implantable cardiac stimulation device of claim 12, wherein the atrial delay time is between about 180 milliseconds and 300 milliseconds.

14. The implantable cardiac stimulation device of claim 12, wherein the atrial delay timer is additionally configured to time an atrial escape interval following a ventricular event, and wherein the pulse generator is configured to deliver test atrial stimulation pulse at the end of the atrial escape interval.

15. The implantable cardiac stimulation device of claim 1, wherein the atrial delay time is periodically determined to prolong the refractory period of the atrium while avoiding stimulation of the ventricle of the patient's heart resulting from the second atrial stimulation pulse.

16. A method of suppressing fusion beats during capture detection in an implantable cardiac stimulation device, the method comprising the steps of:

generating atrial stimulation pulses at a programmed amplitude level and rate for stimulating a patient's heart;

detecting a presence or an absence of an evoked response following a stimulation pulse, wherein the detected absence of an evoked response indicates a potential occurrence of a fusion beat; and generating, in response to the absence of an evoked response, a first atrial stimulation pulse at a first amplitude level and a second atrial stimulation pulse at a second amplitude level an atrial delay time after the first atrial stimulation pulse, whereby atrial refractoriness is prolonged by the second atrial stimulation pulse and a potential occurrence of subsequent fusion beats is minimized.

17. The method of claim 16, further comprising the step of:

setting the first amplitude level for the first atrial stimulation pulse to a predetermined high level selected to ensure capture of the atrium.

18. The method of claim 16, further comprising the step of:

setting the second amplitude level for the second atrial stimulation pulse to a predetermined high level selected to ensure capture of the atrium.

19. The method of claim 16, further comprising the steps of:

measuring the patient's intrinsic cardiac rate; and generating a test stimulation pulse at a test amplitude level, the test stimulation pulse being delayed by a time period defining a cardiac rate in excess of the patient's intrinsic cardiac rate, whereby the potential occurrence of subsequent fusion beats is further minimized.

20. The method of claim 19, further comprising the steps of:

decreasing the test amplitude level in each subsequent cardiac cycle whenever the presence of an evoked response is detected; and setting the capture threshold level to the test amplitude level plus a safety margin whenever the absence of an evoked response is detected.

21. The method of claim 19, further comprising the step of:

generating at least one stimulation pulse at a predetermined amplitude level to cause capture of the heart following each test stimulation pulse to prolong atrial refractoriness.

22. The method of claim 19, further comprising the steps of:

setting the delay time period to a predetermined maximum value;

sensing, following the delivery of each second atrial stimulation pulse, whether a ventricular depolarization occurred; and decreasing the delay time period by a predetermined amount if a ventricular depolarization was sensed in response to the second atrial pacing pulse.

23. The method of claim 22, wherein the step of decreasing the delay time period is bypassed if the decreasing step would decrease the delay time below a predetermined minimum value.

24. The method of claim 23, wherein the step of setting the delay time period to a predetermined maximum value occurs periodically.

25. The method of claim 22, wherein the step of setting the delay time period to a predetermined maximum value occurs in response to detecting premature atrial contractions.

* * * * *